(12) United States Patent
Masuda et al.

(10) Patent No.: US 9,012,484 B2
(45) Date of Patent: Apr. 21, 2015

(54) CRYSTAL AND PHARMACEUTICAL PREPARATION CONTAINING THE SAME CRYSTAL

(71) Applicants: Pola Pharma Inc., Tokyo (JP); Nihon Nohyaku Co., Ltd., Tokyo (JP)

(72) Inventors: Takaaki Masuda, Kanagawa (JP); Makoto Gotoh, Tokyo (JP); Yoshiyuki Miyata, Tokyo (JP)

(73) Assignees: Pola Pharma Inc., Tokyo (JP); Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 14/019,997

(22) Filed: Sep. 6, 2013

(65) Prior Publication Data

US 2014/0080882 A1    Mar. 20, 2014

(30) Foreign Application Priority Data

Sep. 14, 2012  (JP) ................. 2012-202514
Jun. 24, 2013  (JP) ................. 2013-131504

(51) Int. Cl.
*A61K 31/4178* (2006.01)
*C07D 409/06* (2006.01)

(52) U.S. Cl.
CPC .......... *C07D 409/06* (2013.01); *A61K 31/4178* (2013.01)

(58) Field of Classification Search
USPC ........................................ 514/397
See application file for complete search history.

(56) References Cited

U.S. PATENT DOCUMENTS

| | | | |
|---|---|---|---|
| 5,900,488 | A | 5/1999 | Kodama et al. |
| 8,058,303 | B2 | 11/2011 | Miki et al. |
| 8,268,876 | B2 | 9/2012 | Miki et al. |
| 8,349,882 | B2 | 1/2013 | Kobayashi et al. |
| 8,513,296 | B2 | 8/2013 | Masuda et al. |
| 2009/0030059 | A1 | 1/2009 | Miki et al. |
| 2009/0076109 | A1 | 3/2009 | Miki et al. |
| 2009/0137651 | A1 | 5/2009 | Kobayashi et al. |
| 2010/0168200 | A1 | 7/2010 | Masuda et al. |
| 2010/0173965 | A1 | 7/2010 | Masuda et al. |
| 2010/0204293 | A1 | 8/2010 | Masuda et al. |
| 2010/0210702 | A1 | 8/2010 | Vontz et al. |
| 2012/0022120 | A1 | 1/2012 | Kobayashi et al. |
| 2012/0149745 | A1 | 6/2012 | Kobayashi et al. |
| 2013/0011321 | A1 | 1/2013 | Lee et al. |
| 2013/0011351 | A2 | 1/2013 | Kobayashi et al. |
| 2013/0090365 | A1 | 4/2013 | Kubota et al. |
| 2013/0096187 | A1 | 4/2013 | Kobayashi et al. |

FOREIGN PATENT DOCUMENTS

| | | |
|---|---|---|
| CN | 103012385 A | 4/2013 |
| EP | 0715856 A1 | 6/1996 |
| EP | 2005958 A1 | 12/2008 |
| JP | 09-100279 A | 4/1997 |
| JP | 9-100279 A | 4/1997 |
| JP | 2002-114680 A | 4/2002 |
| WO | WO 2007/102241 A1 | 9/2007 |
| WO | WO 2007/102242 A1 | 9/2007 |
| WO | WO 2007/102243 A1 | 9/2007 |
| WO | WO 2009/031642 A1 | 3/2009 |
| WO | WO 2009/031643 A1 | 3/2009 |
| WO | WO 2009/031644 A1 | 3/2009 |
| WO | WO 2014/041708 A1 | 3/2014 |
| WO | WO 2014/041825 A1 | 3/2014 |
| WO | WO 2014/041846 A1 | 3/2014 |
| WO | WO 2014/042043 A1 | 3/2014 |
| WO | WO 2014/136282 | 9/2014 |

OTHER PUBLICATIONS

Niwano, et al. 1999 "Efficacy of NND-502, a novel imidazole antimycotic agent, in experimental models of *Candida albicans* and *Aspergillus fumigatus* infections" International Journal of Antimicrobial Agents 12: 221-228.
Japanese Office Action issued in corresponding Japanese Application No. 2014-029418, mailed on Jun. 24, 2014.
A General Introduction to New pharmaceutics (revised $3^{rd}$ edition), p. 111 (Apr. 10, 1987).
Granulation handbook, pp. 432-433 (Feb. 10, 1978).
Lecture for Experimental Chemistry (Second series) 2. Separation and Purification, pp. 159-178 and 186-187 (Jan. 25, 1967).
New Pharmaceutics, pp. 102-103 and 232-233 (Apr. 25, 1984).
Pharmaceutics, Basic and Application, pp. 142-145 (Sep. 20, 1977).
U.S. Appl. No. 14/263,293, Masuda et al.
International Search Report and Written Opinion of the International Searching Authority for International Application No. PCT/JP2012/079050, mailed on Mar. 8, 2013.
International Search Report and Written Opinion of the International Searching Authority for corresponding International Application No. PCT/JP2013/074775, mailed on Oct. 31, 2013.

*Primary Examiner* — Samantha Shterengarts
(74) *Attorney, Agent, or Firm* — Knobbe, Martens, Olson & Bear LLP

(57) ABSTRACT

An object is to provide means for improving the solubility of luliconazole. Disclosed is a crystal consisting of luliconazole and short chain alcohol having a number of carbon atom or atoms of 1 to 4.

15 Claims, 1 Drawing Sheet

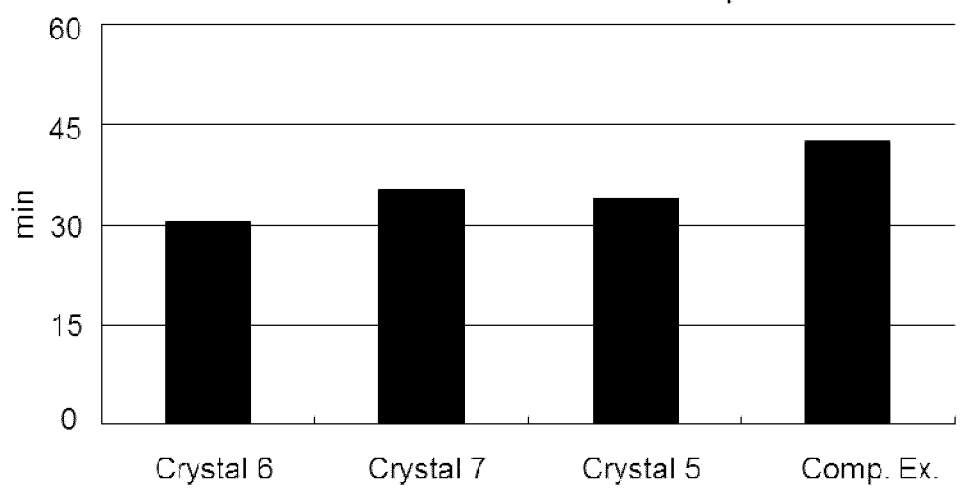

CRYSTAL AND PHARMACEUTICAL PREPARATION CONTAINING THE SAME CRYSTAL

BACKGROUND OF THE INVENTION

1. Field of the Invention

The present invention relates to a crystal of luliconazole and a pharmaceutical preparation containing the crystal.

2. Brief Description of the Related Art

Luliconazole is an antifungal agent which has the structure shown below and which has an excellent action on fungi. At present, luliconazole is widely used as a pharmaceutical or medicine for treatment of infections caused by tinea pedis and tinea corporis, and will be used for treatment of infections caused by tinea unguium. In relation to the pharmaceutical preparation (medicament preparation) of luliconazole, recognized problems to be solved are that luliconazole is converted to stereoisomers, such as the SE isomer and the Z isomer, and that the crystallization of luliconazole occurs immediately after the application (see, for example, WO2007/102241; WO2007/102242; WO2007/102243; WO2009/031642; WO2009/031643; WO2009/031644). These problems limit the effectiveness of luliconazole as an antifungal agent. In particular, as for the isomerization, the present inventors have confirmed that both of the SE isomer and the Z isomer are influenced by the components of the preparation, temperature, and light. A storage condition of 3 weeks at 60° C. is used to evaluate the stability of luliconazole, in which the effects of the above factors are evaluated. To control undesirable conversion to stereoisomers, it has been necessary to shorten the heating step as much as possible in the production of luliconazole.

However, luliconazole has low water solubility. In order to dissolve luliconazole along with other components of a pharmaceutical preparation, it is necessary to perform a heating step. There is a need to develop any means for improving the solubility of luliconazole and shorten the heating time in the heating step. The shortening or reduction of the heating step reduces the generation or formation of any isomer generated or formed in this step and additionally the long-term stability is secured by lowering the initial isomer amount. In other words, the shortening or reduction of the dissolving step results in great improvement in quality.

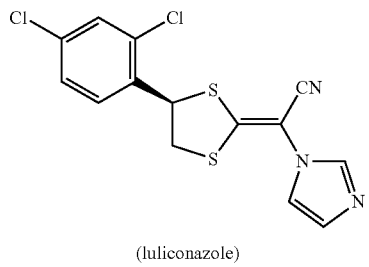 [SMILES: N#C/C(=C1/SC[C@@H](c2ccc(Cl)cc2Cl)S1)n1ccnc1]

(luliconazole)

A method is known, in which luliconazole as an active ingredient is produced by performing recrystallization from ethyl acetate and n-hexane (see, for example, JP9-100279A). However, nothing is known at all about recrystallization with alcohol or any step in which alcohol is added to an active ingredient. Therefore, nothing is known at all about a luliconazole crystal containing short chain alcohol(s) and a composition for an active pharmaceutical ingredient containing luliconazole crystal containing short chain alcohol(s).

SUMMARY OF THE INVENTION

The present invention has been made to address the problems described above, an object of which is to provide means for improving the solubility of luliconazole in order to improve the stability of a pharmaceutical preparation. Thus the basic and novel characteristics of the present invention are improved solubility to shorten heating time, reduction in formation of SE and Z isomers, and improvement in long term stability of the desired RE isomer.

Taking the foregoing circumstances into consideration, the present inventors have repeatedly performed diligent research and effort in order to seek any means for improving the solubility of luliconazole so that the stability of the pharmaceutical preparation is improved. As a result, it has been discovered that a luliconazole crystal containing short chain alcohol(s) and a composition for an active pharmaceutical ingredient containing luliconazole crystal containing short chain alcohol(s) have desirable characteristics, and thus the invention has been completed. That is, the present invention resides in the gist or essential characteristics shown below.

<1> A crystal consisting of luliconazole represented by the following formula and short chain alcohol having a number of carbon atom or atoms of 1 to 4:

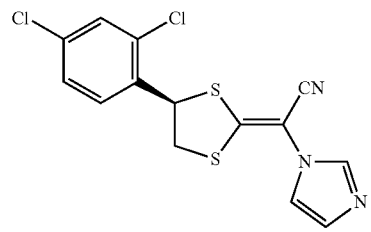

(luliconazole)

<2> The crystal as defined in <1>, wherein a content of the short chain alcohol is 100 to 10,000 ppm with respect to a total amount of the crystal.

<3> The crystal as defined in <1> or <2>, wherein the short chain alcohol is ethanol.

<4> The crystal as defined in any one of <1> to <3>, wherein the crystal is produced by recrystallizing with the short chain alcohol which may contain water, followed by being dried, and added with the short chain alcohol if necessary.

<5> A composition for an active pharmaceutical ingredient, containing the crystal as defined in any one of <1> to <4>.

<6> A pharmaceutical preparation obtained by blending the composition for the active pharmaceutical ingredient as defined in <5>.

<7> A method for producing a pharmaceutical preparation, comprising a step of dissolving, in a solvent, the crystal as defined in any one of <1> to <4> or the composition for the active pharmaceutical ingredient as defined in <5>.

<8> A pharmaceutical preparation produced by the method as defined in <7>.

<9> A pharmaceutical preparation comprising the crystal as defined in <1> to <4> and a pharmaceutically acceptable excipient.

<10> A method of treating a fungal infection by administering an effective amount of a composition comprising the crystal as defined in <1> to <4> or the pharmaceutical preparation defined in <8> or <9> to a subject in need thereof.

<11> The method as defined in <10>, in which the fungal infection is caused by a fungus such as tinea pedis, tinea corporis, tinea versicolor, and tinea unguim.

<12> The method as defined in <10>, in which the fungal infection is athlete's foot, candidiasis, or trichophytosis of hard keratin.

<13> The method as defined in <10>, in which the fungal infection is a dermatomycosis.

<14> The method as defined in <10>, in which luliconazole in the composition is administered at a dose of 0.01 to 1 g per day.

<15> The method as defined in <10>, in which the composition is applied externally.

<16> The method as defined in <10>, in which the composition is applied to a nail.

<17> A method of preparing the luliconazole crystal as defined in <1> by one or more of the following steps:

(a) crystallizing luliconazole from a mixture of ethyl acetate and n-hexane;
(b) recrystallizing the crystal of step (a) with ethanol;
(c) collecting the crystals; and
(d) drying the luliconazole crystals.

<18> The method as defined in <17>, in which the ethanol contains water.

According to the present invention, it is possible to provide means for improving the solubility of luliconazole.

BRIEF DESCRIPTION OF THE DRAWINGS

FIG. 1 shows results of a solubility test for crystals of Examples and a crystal of Comparative Example.

DESCRIPTION OF THE EMBODIMENTS

<1> Crystal of the Present Invention

The crystal of the present invention is characterized in that the crystal contains luliconazole and short chain alcohol(s). In other words, the crystal of the present invention can also be referred to as a crystal composite (complex) containing luliconazole and short chain alcohol(s), or a crystal matrix containing luliconazole and short chain alcohol(s). In this specification, these terms are used synonymously and each mode represented by these terms is included within the scope of the present invention.

The short chain alcohol described above can be preferably exemplified, for example, by alcohol having a straight chain or a side chain and having a number of carbon atom or atoms of 1 to 4 such as methanol, ethanol, isopropyl alcohol, and butanol [for example, methanol, ethanol, 1-propanol (propyl alcohol), 2-propanol (isopropyl alcohol), 1-butanol (n-butyl alcohol), 2-butanol (sec-butyl alcohol), 2-methyl-1-propanol (isobutyl alcohol), and 2-methyl-2-propanol (tert-butyl alcohol)]. In particular, it is preferable to use ethanol. The crystal may contain a single alcohol or two or more alcohols selected from the alcohols as described above. The content of alcohol having a short chain as described above is preferably 100 to 10,000 ppm and more preferably 500 to 5,000 ppm with respect to the total mass of the crystal, for the following reason. That is, if the content is too small, the effect to improve the solubility is not provided in some cases. If the content is too large, the stability of the whole crystal is deteriorated in some cases. The content of luliconazole is preferably not less than 95% by mass and more preferably not less than 99% by mass with respect to the total mass of the crystal.

The crystal as described above can be produced by, for example, recrystallizing luliconazole with a short chain alcohol which may contain water, collecting crystals by filtration, drying the crystals while performing blowing, and allowing the short chain alcohol to be contained as desired, by measuring the amount of the short chain alcohol and adding the short chain alcohol if the amount of the short chain alcohol is not within a preferred range. On the other hand, if the amount of the short chain alcohol is too large, the adjustment can be performed by further performing drying while performing blowing.

The recrystallization may be performed using water-containing alcohol, or water may be used as a poor solvent. In the poor solvent method water, which is in an amount sufficient to cause deposition, is added to an alcohol solution containing luliconazole. In a preferred form, the recrystallization is performed with alcohol containing 10% water, which is preferred in view of the purity to be finally obtained.

The recrystallization can be performed in accordance with any ordinary recrystallization method.

The alcohol as described above may be used together with water. Alternatively, the alcohol as described above may be used in a state in which the alcohol contains water. In both cases, the amount of usable water is preferably exemplified, for example, by 9 to 80%, 30 to 80%, 50 to 75%, or about 70% at the maximum with respect to the total amount of the alcohol which may contain water.

<2> Composition for Active Pharmaceutical Ingredient of the Present Invention

The composition for the active pharmaceutical ingredient of the present invention can contain substances, impurities, and isomers within a range permitted as the active pharmaceutical ingredient, other than luliconazole and the short chain alcohol. However, it is especially preferable that the composition consists essentially of luliconazole and short chain alcohol(s).

The crystal of the present invention and the composition for the active pharmaceutical ingredient obtained as described above have excellent solubility with respect to the solvent. Therefore, the crystal of the present invention and the composition for the active pharmaceutical ingredient are able to suppress, for example, the production of any isomer when forming the pharmaceutical preparation which is produced by performing the production steps including the dissolving step. Therefore, the crystal of the present invention and the composition for the active pharmaceutical ingredient can be used as the raw material for producing the pharmaceutical preparation as described above.

<3> Pharmaceutical Preparation of the Present Invention

The pharmaceutical preparation of the present invention is characterized in that the crystal of the present invention or the composition for the active pharmaceutical ingredient described above is contained therein. The crystal or the composition for the active pharmaceutical ingredient as described above has excellent solubility in a solvent such as ethanol or the like. Therefore, it is preferable to adopt the pharmaceutical preparation which is produced by the production step that includes the dissolving step. Examples of pharmaceutical preparations include but are not limited to a solution, an emulsion, and an ointment of the liquid droplet dispersion type. In particular, the pharmaceutical preparation, in which the content of luliconazole exceeds 5% by mass, requires a considerable period of time to perform the dissolving step. Therefore, the pharmaceutical preparation of the present invention is preferred in view of the shortening or reduction of the dissolution time. The preferred content of luliconazole is 0.1 to 30% by mass with respect to the total amount of the pharmaceutical preparation. More preferably, the content of luliconazole is 0.5 to 15% by mass. Of course, when the pharmaceutical preparation is processed into an oral administration agent such as a tablet or the like, the rate of dissolution is excellent, which is preferred. The oral administration pharmaceutical preparation as described above also belongs to the pharmaceutical preparation of the present invention.

The time required for the dissolving step depends on, for example, the processing condition (treatment condition) and the content of luliconazole in the pharmaceutical preparation as well. However, the time required for the dissolving step, which is required when the crystal of the present invention or the composition for the active pharmaceutical ingredient is used in the dissolving step to prepare, for example, a pharmaceutical preparation in which the content of luliconazole is 0.1 to 30% by mass with respect to the total amount of the pharmaceutical preparation, may be not more than 80%, preferably not more than 75%, and more preferably not more than 70% as compared with the time which is required for the dissolving step when any conventionally available luliconazole is used.

The pharmaceutical preparation of the present invention can be produced by performing the process or treatment in accordance with any ordinary method while appropriately adding thereto, for example, solvent, coloring agent, antioxidant, chelating agent, emulsifier/dispersing agent, solubilizing agent, disintegrating agent, excipient, binding agent, coating agent, and taste/odor-correcting agent other than the crystal of the present invention or the composition for the active pharmaceutical ingredient.

The pharmaceutical preparation of luliconazole of the present invention obtained as described above is characterized in that the amounts of isomers are suppressed in relation to the initial values obtained immediately after the production of luliconazole. The amounts of isomers (SE isomer, Z isomer), which are obtained in relation to the initial values provided immediately after the production of luliconazole, may be as follows as compared with the case in which the crystal having such a crystal habit that the (11-1) plane is the specific growth surface produced by conventional methods such as a method by recrystallizing from n-hexane-ethyl acetate is used. That is, for example, in the case of the SE isomer, the amount of isomer may be not more than 80%, preferably not more than 70%, and more preferably not more than 60%. In the case of the Z isomer, the amount of isomer may be not more than 70%, preferably not more than 60%, and more preferably not more than 50%. In the case of the sum of those of the SE isomer and the Z isomer, the sum may be not more than 80%, preferably not more than 70%, and more preferably not more than 60%.

In particular, there is a high possibility that the isomers as described above may be produced during the dissolving step in the solvent. Therefore, the luliconazole crystal or the composition for the active pharmaceutical ingredient is especially preferred as the active ingredient for the pharmaceutical medicament preparation to be produced while including the step as described above.

The pharmaceutical preparation or the pharmaceutical composition of the present invention is preferably used to treat or cure a disease caused by any fungus or prevent the worsening of the disease by utilizing the characteristic of luliconazole. The pharmaceutical preparation of the present invention is also preferably used to treat the disease caused by any protozoa such as *Trichomonas vaginalis* or prevent the deterioration of the disease. The disease caused by any fungus can be exemplified by tinea pedis such as athlete's foot, tinea corporis such as candidiasis and tinea versicolor, and trichophytosis of hard keratin portion such as tinea unguium. It is especially preferable to use the pharmaceutical preparation or the pharmaceutical composition of the present invention for treating a disease of the hard keratin portion such as tinea unguium, because the effect thereof is remarkable. The effect of the pharmaceutical composition of the present invention is expressed on the nail especially preferably. However, the effect is also exerted on any ordinary dermatomycosis. Therefore, the pharmaceutical composition, which is directed to dermatomycosis and which fulfills the construction of the present invention, also belongs to the technical scope of the present invention. The dermatomycosis as described above can be exemplified, for example, by the tinea pedis and the trichophytosis of the propagation in horny substance type, the trichophytosis of the propagation in horny substance type appearing, for example, in the heel and being included in the tinea pedis. As for the dermatomycosis described above, it is preferable to apply a luliconazole crystal preparation according to embodiments of the invention to trichophytosis propagated in horny substance as ordinary antifungal agents or drugs have little effect. However, the effect of luliconazole crystal preparation according to embodiments of the invention is remarkable.

The mode of use can be appropriately selected while considering, for example, the body weight, the age, the sexuality, and the symptoms or condition of the patient. However, in the case of an adult, it is preferable to administer luliconazole in an amount of 0.01 to 1 g per day in ordinary cases. Reference can be made to the amount of use of luliconazole ordinarily used for the disease caused by any fungus.

For example, in the case of any preparation for external use, it is possible to apply an appropriate amount to the disease portion once or several times a day. It is preferable that the treatment as described above is performed every day. In particular, in the case of the tinea unguium, luliconazole as the active ingredient in an amount that cannot be brought about by any ordinary pharmaceutical preparation can be transferred into the nail. Accordingly, the tinea unguium can be cured by means of only the external administration alone without the need for oral administration of an antifungal agent for a long period of time. Further, the recurrence and the reinfection cause great problems, particularly for infections due to tinea unguium. However, it is possible to avoid the recurrence and reinfection as described above by administering the pharmaceutical composition of the present invention for 1 week to 2 weeks after the disappearance of symptoms. In such a mode, the pharmaceutical composition of the present invention has a preventive effect for recurrence or reinfection.

EXAMPLES

The present invention will be explained in further detail below as exemplified by Examples. However, the present invention is not limited to Examples described below.

Example 1

Luliconazole, which was obtained by performing recrystallization from a mixture solution of ethyl acetate and n-hexane, was used to perform recrystallization from ethanol containing 10% water. Crystals were collected by filtration, followed by being dried in a desiccator in which phosphorus pentaoxide was placed. The ethanol content of this sample was measured by means of gas chromatography. As a result, the ethanol content was 3,500 ppm, and hence ethanol was contained. Therefore, it was confirmed that this sample was the crystal (Crystal 1) of the present invention. Luliconazole (Raw Material 1), which was the raw material of the crystal of the present invention and which was obtained by performing recrystallization from ethyl acetate and n-hexane, had the content of ethanol which was not more than the detection limit.

The single crystal X-ray structure analysis was performed for Crystal 1 of the present invention (name of machine type of apparatus: RU-H2R, name of manufacturer: Rigaku Corporation, Condition: X-ray source: CuKα, measurement temperature: 26° C., tube voltage: 50 kV, tube current: 180 mA, 2θmax: 150.0°, structure analysis method: direct method (SHELX 86)). The crystal system, the space group, the lattice constant, and the R factor, which were obtained from measured values, were as follows.

Crystal system: monoclinic crystal

Space group: $P2_1$

Lattice Constant:

a=9.0171(9) Å b=8.167(1) Å c=10.878(1) Å

β=95.917(9)°

R Factor:

R=0.046

$R_w$=0.047

Example 2

An elution test (stirring condition: 50 rpm) was performed for Raw Material 1 (Crystal of Comparative Example) and Crystal 1 of Example 1 to investigate the elution dynamics. After confirming the dissolution of all crystals, the Z isomer and the SE isomer, which were isomers produced in the solution, were analyzed and quantitatively measured by means of HPLC.

In the elution test, 500 mL of anhydrous ethanol was used as the solvent, wherein 1 g of the sample was dissolved at room temperature while stirring, and the time, which was required for the dissolution, was simultaneously measured. Results are shown in Table 1. Accordingly, it is understood that the time, which is required for the dissolution, is short for Crystal 1, and thus the production of the Z isomer and the SE isomer as the isomers is suppressed in the dissolving step.

The condition for HPLC was as follows. Column: CHIRALCEL OD-RH 4.6×150 mm, column temperature: 35° C., mobile phase: mixture solution of methanol/2% aqueous solution of potassium hexafluorophosphate (85:15, v/v), flow rate: 0.6 mL/min., detection: 295 nm).

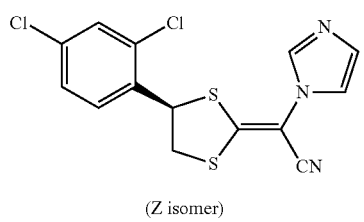

(Z isomer)

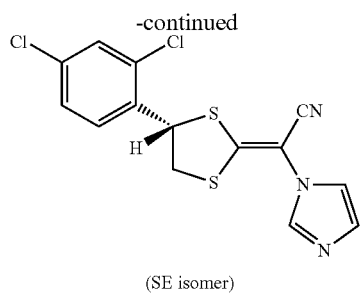

(SE isomer)

TABLE 1

| Sample | Time required until dissolution (minutes) | Amount of generation of Z isomer (%) | Amount of generation of SE isomer (%) |
| --- | --- | --- | --- |
| Crystal 1 | 200 | 0.06 | 0.06 |
| Crystal of Comp. Ex. | 300 | 0.13 | 0.09 |

Example 3

The alcohol contents of crystals (Crystals 2, 3) obtained by changing the recrystallization condition of Example 1 were measured, and the state of dissolution in ethanol was also observed with the naked eye. Results are shown in Table 2. Crystal 2 and Crystal 3 are the crystals of the present invention, wherein the dissolution state was satisfactory as well. That is, the solubility is especially improved when ethanol is contained at a concentration of not less than 1,000 ppm.

TABLE 2

| Sample | Recrystallization solvent | Ethanol content | Solubility |
| --- | --- | --- | --- |
| Crystal 2 | ethanol containing 75% water | 3,700 ppm | solubility is satisfactory |
| Crystal 3 | ethanol containing 50% water | 1,278 ppm | solubility is satisfactory |

Example 4

A pharmaceutical preparation (lotion preparation) was manufactured by using Crystal 1 of the present invention. That is, formulation components were heated, stirred, and solubilized. After confirming the solubilization, agitation and cooling were quickly performed to obtain a pharmaceutical preparation according to embodiments of the invention. The time required for the dissolution was not more than 5 minutes. This sample was measured for the Z isomer and the SE isomer. The content of the Z isomer was not more than the detection limit, and the SE isomer was 0.03%. It was confirmed that the production was successfully performed without deteriorating the stability.

TABLE 3

| Component | % by mass |
| --- | --- |
| Luliconazole | 1 |
| N-methyl-2-pyrrolidone | 8 |
| Diisopropyl adipate | 5 |

TABLE 3-continued

| Component | % by mass |
| --- | --- |
| 1,3-Butanediol | 30 |
| Water | 10 |
| Ethanol | 46 |

Example 5

The alcohol content of Crystal 4 obtained by changing the recrystallization condition of Example 1 was measured, and the state of dissolution in ethanol was also compared with those of Crystal of Comparative Example of Example 1 and Crystal 3 to compare the solubility.

Crystal 4 was prepared as follows. That is, 150 mL of ethanol was added to 5 g of luliconazole, followed by being refluxed and solubilized. Cooling was performed slowly to a temperature of 70° C. while stirring, and this temperature was retained for 20 minutes. After that, 20 mL of water was added thereto, followed by stirring and cooling. Deposited crystals were collected by filtration, followed by drying for 48 hours while performing blowing at 30° C. to obtain Crystal 4 of the present invention. This sample had an ethanol content of 262 ppm. As for the solubility, there is given Comparative Example<<Crystal 4<Crystal 3. It is understood that the effect of the present invention is provided in the case of Crystal 4. Accordingly, the data suggests that the lower limit value permitted for alcohol is 100 ppm.

Example 6

The alcohol content of Crystal 5 obtained by changing the recrystallization condition of Example 1 was measured, and the state of dissolution in ethanol was also compared with those of Crystal of Comparative Example of Example 1 and Crystal 2 to compare the solubility.

Crystal 5 was prepared as follows. That is, 150 mL of ethanol was added to 5 g of luliconazole, followed by being refluxed and solubilized. Cooling was performed slowly to a temperature of 80° C. while stirring, and this temperature was retained for 5 minutes. 15 mL of water was gradually added thereto, followed by being stirring and cooling. Deposited crystals were collected by filtration, followed by drying for 24 hours while performing blowing at 30° C. to obtain Crystal 5 of the present invention. This crystal had an ethanol content of 7029 ppm. As for the solubility, there is given Crystal of Comparative Example<<Crystal 2=Crystal 5.

Example 7

The alcohol content of Crystal 6 obtained by changing the recrystallization condition of Example 1 was measured, and the state of dissolution in ethanol was also compared with those of Crystal of Comparative Example of Example 1, Crystal 4, and Crystal 3 to compare the solubility.

Crystal 6 was prepared as follows. That is, 200 mL of ethanol was added to 5 g of luliconazole, followed by being refluxed and solubilized. Cooling was performed slowly to a temperature of 70° C. while stirring, and this temperature was retained for 10 minutes. After that, 10 mL of water was added thereto, followed by stirring and cooling. Further, 10 mL of water was added, and deposited crystals were collected by filtration, followed by drying for 48 hours while performing blowing at 30° C. to obtain Crystal 6 of the present invention. Crystal 6 had an ethanol content of 403 ppm. As for the solubility, there is given an order of Crystal of Comparative Example<<Crystal 4=Crystal 6<Crystal 3.

Example 8

The alcohol content of Crystal 7 obtained by changing the recrystallization condition of Example 1 was measured, and the state of dissolution in ethanol was also compared with those of Crystal of Comparative Example of Example 1 and Crystal 5 to compare the solubility.

Crystal 7 was prepared as follows. That is, 200 mL of aqueous solution of 90% ethanol was added to 5 g of luliconazole, followed by being refluxed and solubilized. Cooling was performed slowly to a temperature of 80° C. while stirring, and this temperature was retained for 5 minutes. 15 mL of water was gradually added thereto, followed by stirring and cooling. Deposited crystals were collected by filtration, followed by drying for 24 hours while performing blowing at 30° C. to obtain Crystal 7 of the present invention. Crystal 7 had an ethanol content of 4146 ppm. As for the solubility, there is given Crystal of Comparative Example<<Crystal 5=Crystal 7.

From the results of Examples 1, 3, and 5 to 7, it is understood that the sample, which has the high alcohol content and which is included in the crystal of the present invention, is obtained by adding the poor solvent in the high temperature state and performing the recrystallization in accordance with the poor solvent method (Example 6). Further, it is also understood that the alcohol content tends to increase when the shock of the addition of the poor solvent is mitigated (Example 8). It is also understood that the alcohol content is approximate to the lower limit value when the recrystallization is performed with the alcohol/water mixture solvent having the high water content or when the recrystallization is performed by adding the poor solvent at the low temperature (Examples 5, 7).

Example 9

The solubility was investigated on the basis of the method of Example 2 for Crystals 5 to 7 and Crystal of Comparative Example (stirring condition: 200 rpm). The time required for the dissolution is shown in FIG. 1. Accordingly, it is understood that any one of the crystals of the embodiments of the invention described above has better solubility than the crystal of Comparative Example.

Example 10

The alcohol content (content of alcohol used in recrystallization) of compositions obtained by changing the recrystallization condition of Example 1 was measured, and the state of dissolution in ethanol was also observed with the naked eye. The results are shown in Table 4.

Crystal 8 was recrystallized by procedures as described below. That is, 150 mL of methanol was added to 10 g of luliconazole, followed by heating to 60° C. and solubilization while stirring. 50 mL of water heated to 70° C. in advance was added thereto, followed by being stirred and mixed. Crystals were deposited by stirring while cooling in cooling water at 5° C., followed by standing for 30 minutes. After that, crystals were collected by filtration, followed by drying for 48 hours while performing blowing at 40° C. to obtain Crystal 8 of the present invention. Crystal 9 was obtained by the same procedures as described above except that 50 mL of methanol was added to 10 g of luliconazole, and 150 mL of water was added thereto. Crystal 10 was obtained by the same procedures as described above except that 100 mL of methanol was added to 10 g of luliconazole, and 100 mL of water was added thereto. Crystal 11 was obtained by the same procedures as described above except that 200 mL of 2-propanol was added to 10 g of luliconazole, and no water was added thereto. All of the crystals are embodiments of the crystals of the present invention, wherein the dissolution state was satisfactory as well. That is, it is understood that the solubility is especially improved when an alcohol having a number of carbon atom or atoms of 1 to 4 is contained by not less than 500 ppm, more preferably not less than 1,000 ppm.

TABLE 4

| Sample | Recrystallization solvent | Alcohol content | Solubility |
| --- | --- | --- | --- |
| Crystal 8 | methanol containing 25% water | 878 ppm | solubility is satisfactory |
| Crystal 9 | methanol containing 75% water | 3,530 ppm | solubility is satisfactory |
| Crystal 10 | methanol containing 50% water | 2,275 ppm | solubility is satisfactory |
| Crystal 11 | 2-propanol | 746 ppm | solubility is satisfactory |

Example 11

Effects of an active ingredient containing alcohol were examined by utilizing crystal 10. Crystal, which was obtained by performing recrystallization from a mixture solution of ethyl acetate and n-hexane and which contained no alcohol, was used as a comparative example (comparative crystal). Direct effects of luliconazole were investigated by utilizing *Trichomonas vaginalis* (clinically isolated strain). Samples were prepared such that 5.08 mg of comparative crystal was added in "*Trichomonas* medium F" (Fuji Pharma), 5.08 mg of crystal 10 was added in the medium, and 5 μL of water was added in the medium (control). 200 mL of culture solution containing $3.93 \times 10^5$ cells/mL of *Trichomonas vaginalis* was added to each of the samples, followed by culturing for 4 days at 37° C. After that, cells of *Trichomonas* were counted on a hemocytometer. The results are shown in Table 5. Between these three samples, significant difference was confirmed at a critical value of not more than 1%. From this result, it is understood that crystal of the present invention has excellent antiprotozoal effect.

TABLE 5

|  | Average | SD |
| --- | --- | --- |
| Crystal 10 | 256000 | 115238.9 |
| Comparative crystal | 376000 | 77974.35 |
| Control | 512000 | 76941.54 |

Example 12

According to the formulation described in the following Table 6, tablet was prepared, and its hardness was measured. PTB311 (Pharma Test GmbH) was used as a measurement apparatus for hardness. Condition of tableting was performed at tableting pressure of 1 ton/cm² by utilizing 9 mmφ of a mortar and mallet. Comparative example was prepared by performing same procedures as described above by using comparative crystal. Averages of 6 tablets of each sample are shown in Table 7. From this result, it is understood that crystal of the present invention has high hardness and has excellent physical stability. Accordingly, it is assumed that a tablet having high hardness can be obtained by utilizing the active ingredient containing alcohol since the active ingredient containing alcohol has strong affinity between the active ingredients.

TABLE 6

| Component | % by mass |
| --- | --- |
| Lactose | 50 |
| Luliconazole | 50 |

TABLE 7

| Tablet | Hardness (N) |
| --- | --- |
| Crystal 10 | 73.7 ± 4.2 |
| Comparative crystal | 29.1 ± 3.0 |

INDUSTRIAL APPLICABILITY

The present invention can be applied to pharmaceuticals.

While the invention has been described in detail with reference to preferred embodiments thereof, it will be apparent to one skilled in the art that various changes can be made, and equivalents employed, without departing from the scope of the invention. Each of the aforementioned documents, including the foreign priority document, JP 2012-202514 and JP 2013-131504, is incorporated by reference herein in its entirety.

What is claimed is:

1. A crystal composite consisting of luliconazole represented by the following formula and 100 to 10,000 ppm of short chain alcohol having a number of carbon atom or atoms of 1 to 4 with respect to a total amount of the crystal composite, wherein the crystal is characterized by crystal system of monoclinic crystal, space group of $P2_1$, lattice constant of a=9.0171(9) Å, b=8.167(1) Å, c=10.878(1) Å, β=95.917(9)°, R factor of R=0.046, $R_w$=0.047:

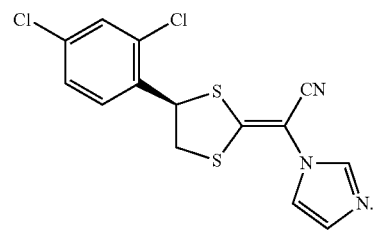

(luliconazole)

2. The crystal composite according to claim 1, wherein the short chain alcohol is ethanol.
3. The crystal composite according to claim 1, wherein the crystal is produced by recrystallizing with the short chain alcohol which may contain water, followed by being dried, and added with the short chain alcohol if necessary.
4. An active pharmaceutical ingredient, containing the crystal composite as defined in claim 1.
5. A method for producing a pharmaceutical preparation, comprising a step of dissolving, in a solvent, the crystal as defined in claim 1.

6. A method of treating a fungal infection comprising administering an effective amount of a composition comprising the crystal of claim 1 to a subject in need thereof.

7. The method of claim 6, wherein the fungal infection is caused by a fungus selected from the group consisting of tinea pedis, tinea corporis, tinea versicolor, and tinea unguim.

8. The method of claim 6, wherein the fungal infection is selected from the group consisting of athlete's foot, candidiasis, and trichophytosis of hard keratin.

9. The method of claim 6, wherein the fungal infection is a dermatomycosis.

10. The method of claim 6, wherein luliconazole in the composition is administered at a dose of 0.01 to 1 g per day.

11. The method of claim 6, wherein the composition is applied externally.

12. The method of claim 11, wherein the composition is applied to a nail.

13. A method of preparing the luliconazole crystal of claim 1 comprising:
   (a) crystallizing luliconazole from a mixture of ethyl acetate and n-hexane;
   (b) recrystallizing the crystal of step (a) with ethanol;
   (c) collecting the crystals; and
   (d) drying the luliconazole crystals.

14. The method of claim 13, wherein the ethanol contains water.

15. An active pharmaceutical ingredient, containing the crystal composite as defined in claim 1 and a substance within a range permitted as the active pharmaceutical ingredient.

* * * * *